us 008969595B2

(12) United States Patent
Uppara et al.

(10) Patent No.: US 8,969,595 B2
(45) Date of Patent: Mar. 3, 2015

(54) METHOD OF MAKING DIACETAL COMPOUND IN AQUEOUS MEDIUM

(75) Inventors: Parasu Veera Uppara, Maharashtra (IN); Pavankumar Aduri, Maharashtra (IN); Mangesh Sakhalkar, Maharashtra (IN); Uday Ratnaparkhi, Maharashtra (IN)

(73) Assignee: Reliance Industries Limited, Mumbai, Maharashtra (IN)

( * ) Notice: Subject to any disclaimer, the term of this patent is extended or adjusted under 35 U.S.C. 154(b) by 0 days.

(21) Appl. No.: 13/978,579

(22) PCT Filed: Feb. 28, 2011

(86) PCT No.: PCT/IN2011/000122
§ 371 (c)(1),
(2), (4) Date: Jul. 8, 2013

(87) PCT Pub. No.: WO2012/095857
PCT Pub. Date: Jul. 19, 2012

(65) Prior Publication Data
US 2013/0281716 A1    Oct. 24, 2013

(30) Foreign Application Priority Data
Jan. 10, 2011  (IN) .............................. 80/MUM/2011

(51) Int. Cl.
*C07D 493/00* (2006.01)
*C07D 493/04* (2006.01)

(52) U.S. Cl.
CPC .................................... *C07D 493/04* (2013.01)
USPC ........................................................ 549/364

(58) Field of Classification Search
CPC ..................................................... C09D 493/04
USPC ........................................................ 549/364
See application file for complete search history.

(56) References Cited

U.S. PATENT DOCUMENTS

| | | | |
|---|---|---|---|
| 3,721,682 A | 3/1973 | Murai et al. |
| 4,267,110 A | 5/1981 | Uchiyama |
| 4,429,140 A | 1/1984 | Murai et al. |
| 4,562,265 A | 12/1985 | Machell |
| 4,902,807 A | 2/1990 | Kobayashi et al. |
| 5,023,354 A | 6/1991 | Salome et al. |
| 5,104,840 A | 4/1992 | Chauvin et al. |
| 5,731,474 A | 3/1998 | Scrivens et al. |
| 5,892,124 A | 4/1999 | Olivier et al. |
| 6,500,964 B2 | 12/2002 | Lever et al. |
| 6,527,977 B2 | 3/2003 | Helber et al. |
| 6,573,405 B1 | 6/2003 | Abbott et al. |
| 7,183,433 B2 | 2/2007 | Abbott et al. |
| 7,196,221 B2 | 3/2007 | Abbott et al. |
| 2002/0137953 A1 | 9/2002 | Lever et al. |
| 2005/0147889 A1 | 7/2005 | Ohzuku et al. |
| 2006/0183654 A1 | 8/2006 | Small |
| 2008/0221353 A1 | 9/2008 | Tsunashima |
| 2008/0307703 A1 | 12/2008 | Dietenberger et al. |
| 2009/0247432 A1 | 10/2009 | Miller |
| 2012/0232150 A1 | 9/2012 | Mobashery et al. |

FOREIGN PATENT DOCUMENTS

| | | |
|---|---|---|
| CN | 1858048 A | 11/2006 |
| CN | 1903857 | 1/2007 |
| CN | 101440025 A | 5/2009 |
| CN | 101544628 A | 9/2009 |
| CN | 101723852 A | 6/2010 |
| JP | 2009057297 | 3/2009 |
| KR | 20080003855 | 1/2008 |
| WO | 00/41809 | 7/2000 |
| WO | 02/26701 | 4/2002 |
| WO | 2006/007703 | 1/2006 |
| WO | 2006/044187 | 4/2006 |
| WO | 2007/023814 | 3/2007 |
| WO | 2012/095858 | 7/2012 |

OTHER PUBLICATIONS

International Search Report of PCT/IN2011/000122, date of mailing Oct. 20, 2011.
Olivier-Bourbigou, H., et al., Applied Catalysis A: General, 373, 1-56, 2010.
Deetlefs, M., et al., J. Physical Chemistry B. 110, 12055-12061, 2006.
Canongia Lopez, J. N. and Padua, A. A. H., J. Physical Chemistry B. 110, 3330-3335, 2006.
International Search Report of PCT/IN2011/000120, dated Oct. 20, 2011, 5 pages.
International Search Report of PCT/IN2011/000123, dated Oct. 27, 2011, 3 pages.
Angew. Chem. Int. Ed., Ionic Liquids—New "Solutions" for Transition Metal Catalysis, 2000, 39, 3772-3789.
Non-Final Office Action for U.S. Appl. No. 13/936,393 dated Oct. 10, 2013, 8 pages.
Non-Final Office Action for U.S. Appl. No. 13/936,393 dated Jun. 19, 2014, 8 pages.
Non-Final Office Action for U.S. Appl. No. 13/936,436 dated Oct. 9, 2013, 8 pages.

*Primary Examiner* — Noble Jarrell
*Assistant Examiner* — Raymond Covington
(74) *Attorney, Agent, or Firm* — Collard & Roe, P.C.

(57) ABSTRACT

This invention is directed to a process for preparation of acetal derivatives, 1,3:2,4-bis(3,4-dimethylbenzylidene)sorbitol (DMDBS) and 1,3:2,4-bis(4-methylbenzylidene)sorbitol (MDBS) by carrying out a dehydrocondensation reaction between an aldehyde and an alditol using an aqueous ionic fluid as the acid catalyst.

12 Claims, No Drawings

METHOD OF MAKING DIACETAL COMPOUND IN AQUEOUS MEDIUM

CROSS REFERENCE TO RELATED APPLICATIONS

This application is the National Stage of PCT/IN2011/000122 filed on Feb. 28, 2011, which claims priority under 35 U.S.C. §119 of Indian Application No. 80/MUM/2011 filed on Jan. 10, 2011, the disclosures of which are incorporated by reference. The international application under PCT article 21(2) was published in English.

FIELD OF INVENTION

This invention relates to a method of producing alditol acetals in an aqueous ionic fluid.

BACKGROUND OF THE INVENTION

The acetal compound is the reaction product of an alditol and benzaldehyde. Alditol acetals, such as 1,3:2,4-bis(4-methylbenzylidene)sorbitol (MDBS) and 1,3:2,4-bis(3,4-dimethylbenzylidene)sorbitol (DMDBS) derivative compounds are known compounds which find their utility as an additive in polypropylene. Acetals of substituted and unsubstituted aldehydes are also known to be useful as nucleating agents, gelling agents, processing aids, and strength modifiers in polyolefin resins, polyester resins, deodorant, and antiperspirant compositions; hydrocarbon fuels and paints.

Acetal alditols are typically prepared by the condensation reaction of an aromatic aldehyde with an alditol containing 6 carbon atoms like sorbitol. For MDBS and DMDBS structures, such reactions involve two moles of the aldehyde and one mole of an alditol.

Several methods for the preparation of acetal alditols have been reported in U.S. Pat. No. 4,267,110, U.S. Pat. No. 3,721,682, U.S. Pat. No. 4,429,140; U.S. Pat. No. 4,562,265; U.S. Pat. No. 4,902,807; U.S. Pat. No. 5,023,354; U.S. Pat. No. 5,731,474 and U.S. Pat. No. 6,500,964.

The hitherto reported methods suffer from several shortcomings. Majority of the earlier known processes employ various organic solvents which necessitates high temperature for carrying out the reaction thereby increasing the cost component. Furthermore, most of solvents are very expensive and they too render the process un-economical.

Attempts have been made in the past to overcome the above mentioned shortcomings by employing the acidic catalyst for improving the yield and the versatility (ability to employs variety of substituted aldehydes) the process.

The presently known processes for the preparation of acetals which employ acidic catalysts still suffer from several limitations. Though mineral acids serve as good catalysts for the acetalization process, they are very corrosive in nature. Furthermore, the final product resulting from such processes needs to be purified by neutralizing the residual free acid. Though the yields offered by all teachings are acceptable for the practical purposes, all the methods are not effective from the perspective of versatility, environmentally friendliness, energy efficient, reliability, cost-effective, and safe production.

Ionic systems, which are examples of viscous molten salts, have a number of interesting and useful properties, and have utility, for example, as highly polar solvents, and catalyst in synthetic chemistry. They also have been found to be useful in applications in various fields such as electrochemistry, synthesis of chemical compounds, dyes, batteries, fuel cells, photovoltaic devices, electro-deposition processes, semi conductor cleaning, pyrolysis, gasification, in applications involving cellulose dissolution, for the electroplating of metals as described, for example in U.S. Pat. No. 6,573,405, U.S. Pat. No. 7,183,433, U.S. Pat. No. 7,196,221, US Patent Appl. No. 2005/0147889, U.S. Pat. No. 6,527,977, US Patent Appl. No. 2008/0307703, US Patent Appl. No. 2006/0183654, US Patent Appl. No. 2009/0247432.

Ionic compounds/liquids prepared from quaternary ammonium salt as one of the ions have been reported in U.S. Pat. No. 5,892,124, U.S. Pat. No. 5,104,840, U.S. Pat. No. 6,573,405, U.S. Pat. No. 7,183,433 and U.S. Pat. No. 7,196,221. Ionic compounds/liquids made from choline chloride and metal salts in particular are also known.

Ionic liquids exhibit very low or no vapour pressure and thus, in contrast to many conventional molecular solvents produce virtually no vapours. They are therefore advantageous from a health, safety and environmental point of view.

Processes for preparation of acetals and di-acetals other than MDBS and DMDBS structures using ionic liquids as catalysts and/or reaction medium have been reported. For example, CN 101440025 discloses a method for preparation of ethylidene ether or ketal which employs N-methyl glyoxaline bisulphate ionic liquid catalyst. Other patents which disclose the use of ionic liquids as catalyst for preparation of acetals other than MDBS and DMDBS structures include CN 101723852, CN 101544628 and CN 1858048.

None of the hitherto reported processes for preparation of MDBS and DMDBS have employed ionic compounds/liquids as catalysts and/or reaction medium. There exists a need for process for preparation of MDBS and DMDBS which uses ionic compounds/liquids as the catalyst and or reaction medium. There also remains a need for a process for preparation of acetals, particularly MDBS and DMDBS which does not employ any expensive solvents and corrosive mineral acids.

DEFINITIONS

As used in the present specification, the following words and phrases are generally intended to have the meanings as set forth below, except to the extent that the context in which they are used indicates otherwise.

The phrase "aqueous ionic fluid" is used herein to refer to the solvate prepared whereby ionic compound is formed in-situ by dissolving the mixture of a hydrogen donor selected from the group consisting of methanesulfonic acid (MSA), para toluenesulfonic acid (PTSA), oxalic acid, citric acid, benzoic acid, maleic acid and tartaric acid and a 'counter ion providing compound' selected from the group consisting of a quaternary ammonium salt, such as choline chloride and a metal salt such as sodium chloride and zinc chloride.

OBJECTS OF THE INVENTION

It is an object of the present invention to provide a process for preparation of alditol acetal derivative compounds in high yields and purity.

It is another object of the present invention to provide a process that allows the preparation of symmetrical and asymmetrical dibenzylidene sorbitol compounds without any limitation.

It is still another object of the present invention to provide a process for preparation of acetal derivatives which is economical.

It is yet another object of the present invention to provide a process for preparation of acetal derivatives which is environment friendly.

It is yet another object of the present invention to provide a process for preparation of acetal derivatives wherein there the final product is devoid of any residual free acid.

It is yet another object of the present invention to provide a process for preparation of acetal derivatives which is safe.

It is a further object of the invention to provide a method which allows the production of monoacetal and diacetal derivatives without the formation of triacetal derivates.

SUMMARY OF INVENTION

In accordance with the present invention there is provided a process for preparation of acetal derivatives selected from the group consisting of 1,3:2,4-bis(4-methylbenzylidene)sorbitol (MDBS), 1,3:2,4-bis(3,4-dimethylbenzylidene)sorbitol (DMDBS) comprising the following steps:
preparing an aqueous ionic fluid;
carrying out dehydrocondensation reaction by adding an aldehyde and an alditol in a mole ratio of 2:1 in the ionic fluid under continuous stirring to form a reaction mixture;
stirring the resultant reaction mixture to maintain the contents in a suspension form; and
discontinuing the stirring of the reaction mixture to allow the mass formed in the reaction mixture to settle;
isolating and purifying the mass by filtering, washing and drying to obtain an acetal derivative without any free acid residue present therein.

Typically, the aqueous ionic fluid acts as a catalyst for the dehydrocondensation reaction.

Additionally, the aqueous ionic fluid acts as a reaction medium for the dehydrocondensation reaction.

Typically, the aqueous ionic fluid comprises an ionic compound formed by the hydrogen bonding between a hydrogen donor selected from the group consisting of methanesulfonic acid (MSA), para toluenesulfonic acid (PTSA), oxalic acid, citric acid, benzoic acid, maleic acid and tartaric acid and a counterion from at least one counter-ion providing compound selected from the group consisting of choline chloride, sodium chloride and zinc chloride.

Typically, the aldehyde is at least one aldehyde selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-Isopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

Typically, the alditol is selected from the group consisting of sorbitol (100%), and iso-propyl sorbitol. Preferably, alditol is an aqueous solution of sorbitol with a concentration in the range of about 40% to about 99%.

Typically, the method step of stirring is carried out for a period in the range of about 6 to 10 hours.

In accordance with one embodiment, the process of the present invention further comprises a method step of adding a surface active agent during the dehydrocondensation reaction; said surface active agent being selected from the group consisting of anionic surface active agent, cationic surface agent and nonionic surface active agent. In accordance with one embodiment, choline chloride, a cationic surface active agent is employed during the dehydrocondensation reaction.

Typically, the method step of preparing an aqueous ionic fluid comprises adding a hydrogen donor and a 'counter ion providing compound' independently in equimolar quantities to water leading to the in-situ formation of an ionic compound in water.

Typically, the hydrogen donor is selected from the group consisting of at least one acid selected from the group consisting of methanesulfonic acid (MSA), para toluenesulfonic acid (PTSA), oxalic acid, citric acid, benzoic acid, maleic acid and tartaric acid.

Typically, the counter ion providing compound is at least one selected from the group consisting of a quaternary ammonium salt and a metal salt.

Typically, the quaternary ammonium salt is choline chloride and the metal salt is at least one selected from the group consisting of zinc chloride and sodium chloride.

DESCRIPTION

In order to overcome the shortcomings of the hitherto reported processes which employ expensive solvents and corrosive mineral acid catalysts for the preparation of acetals, the inventors of the present invention have chosen the specific ionic fluids for the preparation of the acetals, particularly DMDBS and MDBS.

Accordingly, in a first aspect of the present invention there is provided a process for preparation of acetal derivatives particularly, DMDBS and MDBS by dehydrocondensation reaction between an aldehyde and alditol using an aqueous ionic fluid which serves the dual role of a reaction catalyst and a reaction medium, comprising the following steps:
preparing an aqueous ionic fluid;
carrying out the dehydrocondensation reaction by adding an aldehyde and an alditol in a mole ratio of 2:1 in the ionic fluid under continuous stirring to form a reaction mixture;
stirring the resultant reaction mixture to maintain the contents in a suspension form; and
discontinuing the stirring of the reaction mixture to allow the mass formed in the reaction mixture to settle;
isolating and purifying the mass by filtering, washing and drying to obtain an acetal derivative without any free acid residue present therein.

The aqueous ionic fluid comprises an ionic compound formed from the hydrogen bonding between a hydrogen donor and a counter ion which catalyses the dehydrocondensation. Besides, it also serves as a reaction medium for carrying out the reaction. Typically, the method step of preparing an ionic fluid comprises adding a hydrogen donor and a counter ion providing compound independently in equimolar quantities to water leading to the in-situ formation of an ionic compound in water.

Typically, the hydrogen donor is selected from the group consisting of at least one acid selected from the group consisting of methanesulfonic acid (MSA), para toluenesulfonic acid (PTSA), oxalic acid, citric acid, benzoic acid, maleic acid and tartaric acid.

Typically, the counter ion providing compound is at least one selected from the group consisting of a quaternary ammonium salt and a metal salt. Typically, the quaternary ammonium salt is choline chloride. Typically, the metal salt is at least one selected from the group consisting of zinc chloride and sodium chloride.

The counter ion providing compounds provide counter ion that are capable of forming a hydrogen bond in aqueous medium or aqueous-solvent mixture. The ionic compound formation by result of cations and anions connection by hydrogen bond were reported to have supramolecular structural organization (Olivier-Bourbigou, H., et al., Applied Catalysis A: General, 373, 1-56, 2010; Deetlefs, M., et al., J. Physical Chemistry B. 110, 12055-12061, 2006; Canongia Lopez, J. N. and Padua, A. A. H., J. Physical Chemistry B. 110, 3330-3335, 2006). The continuous microdomains structure formed due to the network of hydrogen bond seem to be favorable for catalytic reactions since acid is not available in free form and this will not impart any residual acidity to the final product.

The aldehyde employed in the process of the present invention is at least one selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-Isopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

Typically, the alditol used in accordance with the process of the present invention is selected from the group consisting of sorbitol (100%), and iso-propyl sorbitol. Alternatively, an aqueous solution of sorbitol with a concentration in the range of about 40% to about 99% is used as the alditol.

One notable problem that is frequently encountered in the preparation of the acetals is solubility of the aldehyde component in water. According to the present invention, a quaternary ammonium salt which is capable of forming an ionic compound also serves as cationic surfactant/emulsifier to improve the solubility of reactant (aldehyde) in aqueous medium. Optionally, a surface active agent is added to the reaction mixture during the dehydrocondensation reaction. Typically, choline chloride is used as the surface active agent. Typically, the dehydrocondensation reaction is carried out at a temperature with a range of about 25° C. to about 50° C.

Typically, the method step of stirring is carried out for a period in the range of about 6 to 10 hours.

The inventors of the present invention have surprisingly found out that the product obtained by the process of the present invention was completely free of any residual free acid. The residual free acid in the product is highly undesirable since it promotes the hydrolysis of the end product at high temperature, especially during the drying process.

The process of the present invention is therefore particularly advantageous since it obviates the need for neutralizing residual free acid in the end product thereby reducing the cost and complexity of the process. This demonstrates the utility of the ionic fluids as a catalyst and reaction medium to carry out the acid based dehydrocondensation reactions.

The following examples further illustrate the present invention but are not to be construed as limiting the invention as defined in the claims appended hereto.

Example: 1

Toluene-4-sulphonic acid monohydrate (PTSA), a hydrogen donor (1.9 gms) was mixed with choline chloride (1.4 gms) in equal mole ratio and water was added to the salt mixture and stirred well to prepare ionic fluid.

3,4 dimethyl benzaldehyde and sorbitol in 2:1 mole ratio were added to the ionic compound and stirred to initiate the reaction. The solid mass formed within few minutes of starting the reaction. The stirring speed was increased to keep the mass in suspension condition and reaction was continued for 8 hrs. The solid product was filtered and washed with 100 ml methanol. The white solid product was dried in oven at 95° C. for 2 hrs followed by air dried for 4 hrs for measuring the yield. The yield was found to be 60%.

Example: 2-6

The procedure of example 1 was followed for different hydrogen donor compounds as given in Table 1 with choline chloride.

Example: 7-18

The procedure of example 1 is followed for different hydrogen donors as given in Table 2 and Table 3 with zinc chloride and sodium chloride respectively.

Example: 19-21

The procedure of example 1 was followed except, additional 0.01 moles of choline chloride was added to the water. The yield was found to be 69%. Similarly for PTSA—sodium and zinc chloride systems, the addition of 0.01 moles of choline chloride improved the yields.

TABLE 1

Details of the reactions carried for examples 1-5 for the procedure described in the example

| Example No | Ratio of Sorbitol to Aldehyde | Water, ml | Choline chloride, gm | Hydrogen Donor, (gm) | Reaction Time, Hrs | Yield, % |
|---|---|---|---|---|---|---|
| 1. | 1:2 | 30 | 1.4 | PTSA (1.9) | 8 | 60 |
| 2 | 1:2 | 10 | 0.7 | MSA (0.48) | 6 | 25 |

TABLE 1-continued

Details of the reactions carried for examples
1-5 for the procedure described in the example

| Example No | Ratio of Sorbitol to Aldehyde | Water, ml | Choline chloride, gm | Hydrogen Donor, (gm) | Reaction Time, Hrs | Yield, % |
|---|---|---|---|---|---|---|
| 3 | 1:2 | 30 | 2.8 | Oxalic Acid (1.3) | 8 | 50 |
| 4 | 1:2 | 30 | 4.2 | Citric Acid (2.1) | 10 | 20 |
| 5 | 1:2 | 30 | 1.4 | Benzoic Acid (1.22) | 10 | 33 |
| 6 | 1:2 | 30 | 2.8 | Maleic Acid (1.16) | 10 | 35 |

TABLE 2

Details of the reactions carried out for examples
7-12 with the procedure described in the example 1

| Example No | Ratio of Sorbitol to Aldehyde | Water, ml | Zinc chloride, gm | Hydrogen Donor, (gm) | Reaction Time, Hrs | Yield, % |
|---|---|---|---|---|---|---|
| 7 | 1:2 | 30 | 1.36 | PTSA (3.8) | 8 | 60 |
| 8 | 1:2 | 10 | 0.68 | MSA (0.96) | 6 | 21 |
| 9 | 1:2 | 30 | 1.36 | Oxalic Acid (1.3) | 8 | 40 |
| 10 | 1:2 | 30 | 2.04 | Citric Acid (2.1) | 9 | 20 |
| 11 | 1:2 | 30 | 1.36 | Benzoic Acid (2.44) | 10 | 25 |
| 12 | 1:2 | 30 | 1.36 | Maleic Acid (1.16) | 9 | 30 |

TABLE 3

Details of the reactions carried out for examples
13-18 with the procedure described in the example 1

| Example No | Ratio of Sorbitol to Aldehyde | Water, ml | Sodium chloride, gm | Hydrogen Donor, (gm) | Reaction Time, Hrs | Yield, % |
|---|---|---|---|---|---|---|
| 13 | 1:2 | 30 | 0.58 | PTSA (1.9) | 8 | 60 |
| 14 | 1:2 | 10 | 0.58 | MSA (0.96) | 6 | 18 |
| 15 | 1:2 | 30 | 1.16 | Oxalic Acid (1.3) | 8 | 35 |
| 16 | 1:2 | 30 | 1.74 | Citric Acid (2.1) | 9 | 15 |
| 17 | 1:2 | 30 | 0.58 | Benzoic Acid (1.22) | 10 | 10 |
| 18 | 1:2 | 30 | 0.58 | Maleic Acid (1.16) | 8 | 30 |

TABLE 4

Details of the reactions carried out for examples
19-21 with the procedure described in the example 1

| Example No | Ratio of Sorbitol to Aldehyde | Water, ml | Choline chloride, gm | Hydrogen Donor, (gm) | Reaction Time, Hrs | Yield, % |
|---|---|---|---|---|---|---|
| 19 | 1:2 | 30 | Choline chloride (1.4) | PTSA (1.9) | 8 | 69 |
| 20 | 1:2 | 30 | NaCl (0.58) | PTSA (1.9) | 8 | 65 |
| 21 | 1:2 | 30 | ZnCl$_2$ (1.36) | PTSA (3.8) | 9 | 68 |

While certain embodiments of the inventions have been described, these embodiments have been presented by way of example only, and are not intended to limit the scope of the inventions. Variations or modifications to the design and construction of this invention, within the scope of the invention, may occur to those skilled in the art upon reviewing the disclosure herein. Such variations or modifications are well within the spirit of this invention. The accompanying claims and their equivalents are intended to cover such forms or modifications as would fall within the scope and spirit of the invention.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

The invention claimed is:

1. A process for preparation of acetal derivatives selected from the group consisting of 1,3:2,4-bis(3,4-dimethylbenzylidene) sorbitol (DMDBS) and 1,3:2,4-bis(4-methylbenzylidene) sorbitol (MDBS) comprising the following steps:
   preparing an aqueous ionic fluid by adding a hydrogen donor and a 'counter ion providing compound' independently in equimolar quantities to water;
   carrying out a dehydrocondensation reaction by adding an aldehyde and an alditol in a mole ratio of 2:1 in the ionic fluid under continuous stirring to form a reaction mixture;
   stirring the resultant reaction mixture to maintain the contents in a suspension form; and
   discontinuing the stirring of the reaction mixture to allow the mass formed in the reaction mixture to settle;
   isolating and purifying the mass by filtering, washing and drying to obtain an acetal derivative without any free acid residue present therein.

2. The process as claimed in claim 1, wherein the aqueous ionic fluid acts as a catalyst for the dehydrocondensation reaction.

3. The process as claimed in claim 1, wherein the aqueous ionic fluid acts as a reaction medium for the dehydrocondensation reaction.

4. The process as claimed in claim 1, wherein the aqueous ionic fluid comprises an ionic compound formed by the hydrogen bonding between at least one hydrogen donor selected from the group consisting of methanesulfonic acid (MSA), para toluenesulfonic acid (PTSA), oxalic acid, citric acid, benzoic acid, maleic acid and tartaric acid and at least one counter ion from at least one counter ion providing compound selected from the group consisting of choline chloride, sodium chloride and zinc chloride.

5. The process as claimed in claim 1, wherein the aldehyde is at least one aldehyde selected from the group consisting of unsubstituted benzaldehyde, and substituted aldehydes including benzaldehyde, 4-methylbenzaldehyde, 3-methylbenzaldehyde, 4-propylbenzaldehyde, p-ethylbenzaldehyde, 4-butylbenzaldehyde, 4-Isopropylbenzaldehyde, 4-isobutylbenzaldehyde, 2,4-dimethylbenzaldehyde, 3,4-dimethylbenzaldehyde, 3,5-dimethylbenzaldehyde, 3-methyl-4-methoxybenzaldehyde, 2,4,5-trimethylbenzaldehyde, 3-hex-1-ynylbenzaldehyde, piperonal, 3-hydroxy-5,6,7,8-tetrahydro-2-naphthaldehyde, 3-Methoxy-5,6,7,8-tetrahydro-2-naphthaldehyde, 3-Hydroxy-8-isopropyl-5-methyl-2-naphthaldehyde, 2-naphthaldehyde, 3-methoxybenzaldehyde, 4-methoxybenzaldehyde, 3,4-dimethoxybenzaldehyde, 3-ethoxybenzaldehyde, 4-ethoxybenzaldehyde, 3,4-diethoxybenzaldehyde, 4-allyloxybenzaldehyde, 4-Propoxybenzaldehyde, 4-carboxybenzaldehyde, 3-bromobenzaldehyde, 4-bromobenzaldehyde, 2-chlorobenzaldehyde, 3-chlorobenzaldehyde, 4-chlorobenzaldehyde, 3-fluorobenzaldehyde, 4-fluorobenzaldehyde, 3,4-dichlorobenzaldehyde, 3,5-dichlorobenzaldehyde, 3,5-dibromobenzaldehyde, 3,5-difluorobenzaldehyde, 4-chloro-3-fluorobenzaldehyde, 3-bromo-4-fluorobenzaldehyde, 4-fluoro-3-methyl-, 5,6,7,8-tetrahydro-2-naphthaldehyde, 4-fluoro-3,5-dimethylbenzaldehyde, 4-(trifluoromethyl)benzaldehyde, 3-bromo-4-ethoxybenzaldehyde and mixtures thereof.

6. The process as claimed in claim 1, wherein the alditol is selected from the group consisting of sorbitol (100%), and iso-propyl sorbitol.

7. The process as claimed in claim 1, wherein the alditol is an aqueous solution of sorbitol with a concentration in the range from 40% to 99%.

8. The process as claimed in claim 1, wherein the method step of stirring is carried out for a period in the range of about 6 to 10 hours.

9. The process as claimed in claim 1, further comprising the method step of adding a surface active agent during the dehydrocondesation reaction; wherein the surface active agent is choline chloride.

10. The process as claimed in claim 9, where in the hydrogen donor is selected from the group consisting of at least one acid selected from the group consisting of methanesulfonic acid (MSA), para toluenesulfonic acid (PTSA), oxalic acid, citric acid, benzoic acid, maleic acid and tartaric acid.

11. The process as claimed in claim 1, wherein the counter ion providing compound is at least one selected from the group consisting of a quaternary ammonium salt and a metal salt.

12. The process as claimed in claim 11, wherein the quaternary ammonium salt is choline chloride and the metal salt is at least one selected from the group consisting of zinc chloride and sodium chloride.

\* \* \* \* \*